US009558319B1

(12) United States Patent
Lathrop

(10) Patent No.: US 9,558,319 B1
(45) Date of Patent: Jan. 31, 2017

(54) METHOD FOR DEDUCING A POLYMER SEQUENCE FROM A NOMINAL BASE-BY-BASE MEASUREMENT

(71) Applicant: Electronic Biosciences, Inc., San Diego, CA (US)

(72) Inventor: Daniel K Lathrop, San Diego, CA (US)

(73) Assignee: Electronic Biosciences, Inc., San Diego, CA (US)

( * ) Notice: Subject to any disclaimer, the term of this patent is extended or adjusted under 35 U.S.C. 154(b) by 953 days.

(21) Appl. No.: 13/672,255

(22) Filed: Nov. 8, 2012

Related U.S. Application Data

(63) Continuation of application No. 12/614,782, filed on Nov. 9, 2009, now Pat. No. 8,452,546.

(60) Provisional application No. 61/112,351, filed on Nov. 7, 2008.

(51) Int. Cl.
*G06F 19/22* (2011.01)
*G06F 15/00* (2006.01)
*G06F 19/16* (2011.01)

(52) U.S. Cl.
CPC ..................... *G06F 19/16* (2013.01)

(58) Field of Classification Search
None
See application file for complete search history.

(56) References Cited

U.S. PATENT DOCUMENTS

| 6,015,714 A | 1/2000 | Baldarelli et al. |
| 7,005,264 B2 * | 2/2006 | Su ........................ C12Q 1/6869 435/6.1 |
| 7,238,485 B2 * | 7/2007 | Akeson ............ B01L 3/502707 435/283.1 |
| 7,731,826 B2 | 6/2010 | Hibbs et al. |
| 8,452,546 B1 * | 5/2013 | Lathrop ........... G01N 33/48721 435/6.1 |

OTHER PUBLICATIONS

Branton et al., "*The Potential and Challenges of Nanopore Sequencing*", Nature Biotechnology vol. 26, No. 10, pp. 1146-1153, Oct. 2008.

* cited by examiner

*Primary Examiner* — John S Brusca
(74) *Attorney, Agent, or Firm* — Diederiks & Whitelaw, PLC

(57) ABSTRACT

A method of processing sequencing data obtained with a polymer sequencing system identifies the most likely monomer sequence of a polymer, regardless of stochastic variations in recorded signals. Polymer sequencing data is recorded and two or more distinct series of pore blocking signals for a section of the polymer are recorded. A value is assigned to each series of pore blocking signals to obtain multiple trial sequences. The probability that each of the trial sequences could have resulting in all of trial sequences is calculated to determine a monomer sequence with the highest probability of resulting in all of the trial sequences, termed the first iteration sequence. The first iteration sequence is systematically altered to maximize the combined probability of the first iteration sequence leading to all the trial sequences in order to obtain a most likely sequence of monomers of the polymer.

27 Claims, 7 Drawing Sheets

TCG$_2$ACTAGC$_3$T$_2$AGCA$_2$TCGA$_3$
TCG$_1$ACTAGC$_3$T$_2$AGCA$_2$TCGA$_3$
GTACTG$_3$C$_3$ACTAGCTAGCACGT
GTACTG$_3$C$_3$ACTAGCTAGCACGT
TCG$_2$ CT$_2$AC$_2$AT$_2$CTAGAGATGCAC
TCG$_2$<u>A</u>CT$_2$AC$_2$AT$_2$CTAGAGATGCAC
AGTAC$_2$T$_2$C$_2$G$_2$C$_3$TC$_2$GAC$_2$ACT
AGTAC$_2$T$_2$C$_2$G$_2$C$_4$TC$_1$GAC$_3$ACT
AT$_2$CA$_2$TC$_2$TCA$_2$T$_1$AT$_2$GCAC$_2$TAC
AT$_1$CA$_2$TC$_2$TCA$_3$T$_2$AT$_1$GCAC$_2$TAC
T$_2$CACA$_2$CAGCTGC$_2$ATACGC$_2$G$_3$
T$_2$CACA$_2$CAGCTGC$_2$ATACGC$_2$G$_3$
G$_4$AT$_2$A$_2$CATC$_2$TGC$_1$ACTCA$_2$GC
G$_3$AT$_1$A$_2$CATC$_2$TGC$_2$ACTCA$_2$GC
AGA$_2$T$_2$G$_2$T$_2$CTCGATAGCTCTAT$_1$A
AGA$_2$T$_1$G$_2$T$_3$CTCGATAGCTCTAT$_2$A
ATAGCGATCTCG$_3$A$_2$GCA$_2$GT$_2$GT$_1$
ATAGCGATCTCG$_2$A$_2$GCA$_2$GT$_1$GT$_2$
T$_2$C$_2$A$_2$G$_2$A$_2$C$_2$G$_2$TCG$_2$TAGCAGA
T$_2$C$_2$A$_2$G$_2$A$_2$C$_2$G$_2$TCG$_2$TAGCAGA
GACTCGAGCT$_2$CG$_2$ACGTCA$_3$CAT
GACTCGAGCT$_2$CG$_1$ACGTCA$_3$CAT
ATG$_3$TATATC$_2$TC$_3$GT$_2$CTGAGT
ATG$_3$TAT<u>XX</u>C$_2$TC$_3$GT$_2$CTGAGT
GC$_2$TG$_3$TA$_2$G$_2$A$_3$GCATCTCG$_2$C
GC$_2$TG$_3$TA$_3$G$_2$A$_3$GCATCTCG$_1$C
G$_2$A$_2$TC$_2$A$_2$CAT$_2$CTATCGCTG$_2$A$_2$
G$_2$A$_1$TC$_2$A$_3$CAT$_2$CTATCGCTG$_1$A$_2$
CTA$_2$C$_2$AC$_1$AGACATCTGCG$_3$A$_2$
CTA$_4$C$_1$AC$_2$AGACATCTGCG$_3$A$_2$
TGT$_4$GTCTG$_2$C$_2$TAGC$_2$TACG$_2$A
TGT$_4$GTCTG$_2$C$_2$TAGC$_2$TACG$_2$A
CGA$_3$TCAT$_1$A$_2$G$_2$A$_2$GTCG$_2$AC$_2$GC
CGA$_3$TCAT$_2$A$_2$G$_2$A$_2$GTCG$_3$AC$_2$GC
TC$_4$TACT$_3$AGTA$_4$CA$_2$TCAC
TC$_4$TACT$_3$AGTA$_4$CA$_1$TCAC
T$_3$GATA$_1$CA$_2$TA$_2$CGCGCTAGT$_2$C$_2$
T$_3$GATA$_2$CA$_1$TA$_2$CGCGCTAGT$_2$C$_2$

FIG. 6A $AC_2AT_1ATAGT_3AT_2GCA_2TGT_1GA_1T$
$AC_1AT_2ATAGT_3AT_1GCA_2TGT_2GA_2T$
$TGC_3T_2CA_2TGCACTGT_1GTCATG_2$
$TGC_2T_2CA_2TGCACTGT_2GTCATG_2$
$T_2GC_2GTC_3TATA_2TCATGTGCAT$
$T_2GC_2GTC_2TATA_2TCATGTGCAT$
$TA_2C_2TAGTGA_2CGTACT_2CGAGC_2$
$TA_1C_1TAGTGA_2CGTACT_2CGAGC_2$
$GT_2GACATACA_2G_2T_4ACTCT_2G$
$GT_1GACATACA_2G_2T_4ACTCT_2G$
$CTC_2GTGCGATAT_2AGT_2GCA_3TG$
$CTC_1GTGCGATAT_2AGT_2GCA_3TG$
$GTAGC_2AT_2AGT_2CGCTGACTC_4$
$GTAGC_2AT_2AGT_2CGCTGACTC_4$
$G_2TC_2GTAGTATGTACT_2CACTGA_2$
$G_2TC_2GTAGTATGTACT_2CACTGA_2$
$TACA_3TCG_2ACTG_2AGAGT_1GTG_3$
$TACA_3TCG_2ACTG_3AGAGT_2GTG_3$
$AGTGCAT_2AGATGCGCAC_2GC_2GAT$
$AGTGCAT_2AGATGCGCAC_1GC_3GAT$
$A_2TCGCG_4TAC_2A_2C_2ATCTA_2G$
$A_2TCGCG_3TAC_2A_2C_2ATCTA_2G$
$AGT_2GC_3ATC_2GCT_2G_3CT_2CGC$
$AGT_2GC_3ATC_1GCT_2G_2CT_1CGC$
$CGATATCG_2CTGAG_2C_2TA_2CT_2CA$
$CGATATCG_2CTGAG_2C_2TA_2CT_1CA$
$G_3ATC_3TATA_2GCGACGACGC_3$
$G_3ATC_2TAXX_2GCGACGACGC_3$
$AGAGTG_2CACTA_2C_2A_2TACGTCGA$
$AGXXTG_2CACTA_2C_2A_2TACGTCGA$
$GTACG_3TCG_2C_3G_3C_2TC_3TA$
$GTACG_3TCG_2C_2G_3C_2TC_2TA$
$TAGAGACG_2CTAGA_2GTATG_2AG_2A$
$TAGXXACG_2CTAGA_2GTATG_1AG_2A$
$A_2CAGATAG_2CT_2CAGA_2TAGTG_2A$
$A_2CAGATAG_2CT_2CAGA_1TAGTG_2A$
$CTCT_2A_2TGACGAC_2T_3A_2GCTGC$
$CTXX_2A_2TGACGAC_2T_2A_2GCTGC$

FIG. 6B

$G_2AGC_2GTACGAGAGC_3T_2A_2GCG$
$G_2AGC_2GTACGAGAGC_3T_2A_2GCG$
$C_2ATAG_2C_2TAGATC_2GT_1GT_2C_2G$
$C_2ATAG_2C_2TAGATC_2GT_\underline{2}GT_\underline{1}C_2G$
$ATC_2GCGAGA_2TC_2GCAGATGT_3A$
$ATC_2GCGAGA_2TC_2GCAGATGT_3A$
$ATCATATGCTGCTGCT_4C_3G_2A$
$ATCATATGCTGCTGCT_4C_3G_2A$
$C_3TAGTCATC_3ACT_2CGT_1GTA_3$
$C_3TAGTCATC_3ACT_\underline{3}CGT_\underline{2}GTA_3$
$GC_2GAGATAT_2GA_2TGCTA_2TACTG$
$GC_\underline{1}GAGATAT_2GA_2TGCTA_2TACTG$
$GT_2CTCGTGATG_3CT_2GCACTACA$
$GT_\underline{1}CTCGTGATG_\underline{2}CT_2GCACTACA$
$GC_2ATGCA_2C_2TGT_3CG_3T_2G_2C$
$GC_\underline{1}ATGCA_2C_2TGT_3CG_3T_2G_\underline{1}C$
$ACTA_2GCACG_2CGC\ GCGACA_2GAG$
$ACTA_\underline{1}GCACG_2CGC\underline{T}GCGACA_2GAG$
$GC_2A_3C_2ATCAC_1ATGC_2GC_3TG_2$
$GC_\underline{1}A_\underline{2}C_2ATCAC_\underline{2}ATGC_2GC_\underline{2}TG_2$
$TC_2GCAGCGCTCAG_3ACGA_2CT_2G$
$TC_2GCAGCGCTCAG_3ACGA_2CT_2G$
$GTACA_1C_2ATGCTC_3TGATGC_3GT$
$GTACA_\underline{2}C_2ATGCTC_3TGATGC_\underline{2}GT$
$ACA_3GCGACTA_3TGC_2TC_2T_2CA$
$ACA_3GCGACTA_3TGC_2TC_2T_2CA$
$GAGC_2GCGTG_1TATA_3GAT_2C_3AG$
$GAGC_2GCGTG_\underline{2}TA\underline{XX}_3GAT_2C_3AG$
$CA_2C_2GTAGTGTAC_2GA_4T_2CA_2$
$CA_\underline{1}C_2GTAGTGTAC_2GA_4T_2CA_2$
$GTAGTA_2T_1ATATGTCT_3C_2G_2TCT$
$GTAGTA_2T_1AT\underline{XX}GTCT_3C_2G_2TCT$
$CAT_2ACT_2ACG_2TACG_2ATCACTG_2$
$CAT_\underline{1}ACT_2ACG_\underline{1}TACG_2ATCACTG_\underline{3}$
$TCGTGTGC_2T_2ACGTAG_3AGT_2GT$
$TCGTG\underline{XX}C_2T_2ACGTAG_3AGT_2GT$
$CATG_2AGTCGCGT_2AC_2TAGACTGA$
$CATG_\underline{1}AGTCGCGT_2AC_2TAGACTGA$

FIG. 6C

METHOD FOR DEDUCING A POLYMER SEQUENCE FROM A NOMINAL BASE-BY-BASE MEASUREMENT

CROSS-REFERENCE TO RELATED APPLICATIONS

The present application represents a continuation of U.S. patent application Ser. No. 12/614,782 entitled "Method for Deducing a Polymer Sequence from a Nominal Base-By-Base Measurement" filed Nov. 9, 2009, now U.S. Pat. No. 8,452,546, which claims the benefit of U.S. Provisional Patent Application Ser. No. 61/112,351 entitled "Data Processing Method for Deducing a Polymer Sequence from a Nominal Base-by-Base Measurement" filed Nov. 7, 2008.

STATEMENT REGARDING FEDERALLY SPONSORED RESEARCH OR DEVELOPMENT

This invention was made with government support under Contract No. W911NF-08-C-0046 awarded by the Army Research Office and the Defense Advanced Research Projects Agency and Contract No. 2R44HG004466-02 awarded by the National Institute of Health, specifically, the National Human Genome Research Institute. The government has certain rights in the invention.

SEQUENCE LISTING

The instant application contains a Sequence Listing, which has been submitted as an ASCII text file via EFS-Web and is hereby incorporated by reference in its entirety. The ASCII text file, created on Mar. 8, 2013, is named Sequence-Listing.txt and is 26,639 bytes in size.

BACKGROUND OF THE INVENTION

Extensive amounts of research and money are being invested to develop a method to sequence DNA, (Human Genome Project) by recording the signal of each base as the polymer is passed in a base-by-base manner through a recording system. Such a system could offer a rapid and low cost alternative to present methods based on chemical reactions with probing analytes and as a result might usher a revolution in medicine.

Research in this area to date has focused on the question of developing a measurement system that can record a sufficient signal from each monomer in order to distinguish one monomer from another. In the case of DNA, the monomers are the well-known bases: adenine (A), cytosine (C), guanine (G), and thymine (T). It is necessary that the signals produced by each base be: a) different from that of the other bases, and b) different by an amount that is substantially larger than the internal noise of the measurement system. This aspect of sequencing is fundamentally limited by the specific property of the polymer being probed in order to differentiate the monomers and the signal to noise ratio (SNR) of the measurement device used to probe it.

A separate question is the order in which the monomers are measured. In order to know which monomer (or group of monomers) is being measured, it is necessary to localize the polymer to a precision comparable in length to the monomer itself. Controlling the polymer position and motion at such short length scales is challenging, in particular the polymer is subject to diffusive (Brownian) motion due to the impact of other molecules in solution.

One popular method to limit the polymer motion is to pass it through a nanopore, an approximately cylindrical cavity in a solid substrate with diameter equal to or a little larger than the polymer of interest. For such a nanopore, the polymer motion is effectively in one dimension (1-D) along the axis of the pore, but is still subject to stochastic variations in this 1-D motion due to Brownian effects. Specifically, Brownian motion results in a "random walk" such that the mean square displacement in a given time t is given by 2Dt for a polymer of diffusion constant D. This random motion is added to the imposed translocation motion, resulting in an inherent uncertainty in the number of bases that have passed through the measurement device. For example, for DNA confined within an alpha-hemolysin ($\alpha$HL) protein pore at 15° C., the mean net 1-D motion due to diffusion alone in 100 microseconds ($\mu$s) is approximately 5 bases. Thus, in a notional example in which a given base is measured for 100 $\mu$s, the DNA would on average have moved a linear distance away from its desired position a total of 5 bases in either direction due to diffusion, resulting in, in this example, a segment of the DNA being re-measured or skipped. Such positional errors can occur no matter how sensitive the measurement system is that identifies each base.

Recent discoveries have shown that physical changes such as cooling the electrolyte and changing the viscosity of the electrolyte can reduce the diffusion constant of DNA in $\alpha$HL by a considerable factor. However, even with such measures, methods proposed to sequence DNA by recording the signal of each base in a serial manner are still expected to have sequence order errors exceeding the current benchmark target of 99.99% accuracy. Accordingly, what is needed in order to develop a practical polymer sequencing system from such new approaches is a method to process data in order to reduce the effect of stochastic variations in the polymer position.

SUMMARY OF THE INVENTION

The method of the present invention utilizes a combination of data processing steps to limit the sequencing error produced by stochastic motion of a polymer in solution, and thereby improves the sequencing accuracy of the overall sequencing system. Initially, a polymer sequencing system, such as a nanopore sensing system, is utilized to record sequence data. The input data for the method of the present invention is an observation of the time series recording of the signal produced as a polymer passes through the nanopore of the sensing system. Two or more observations of each section of the polymer to be sequenced are made. The observations can be made by repeatedly measuring the same polymer molecule, by measuring multiple molecules of the same polymer, or by a combination of both methods. The first step in the data processing method of the present invention is to assign a value to each apparent monomer in each of the observations based upon foreknowledge of the signal amplitude produced by each monomer, and a physical model of the underlying process by which the polymer moves through the device. The outcome is a set of M (M$\geq$2) trial sequences, one trial sequence for each observation.

The second step is to assume in turn that each particular trial sequence is true and calculate the total probability that this particular sequence could have resulted in all of the M observations. The total probability is calculated from the known statistics of the underlying stochastic processes that lead to the variations in polymer position. The trial sequence with the highest total probability of resulting in the complete set of observations is chosen as the first iteration.

In the preferred embodiment, a third step comprises systematically altering the first iteration sequence to maximize the combined probability of its leading to the M observations. In the simplest embodiment, it is assumed that all changes are local, involving only one or two adjacent monomers, and at each position a small set of likely changes is evaluated to see if any improves the combined probability, with the probabilities calculated as for the second step. If the combined probability improves, the change is kept and the process continues. This is done consecutively for each monomer position in the first iteration sequence, and then started again from the beginning and repeated until an entire sweep through the positions results in no further statistically relevant improvement.

The invention is not specific to the method used to identify an individual monomer and can in principle be utilized in combination with any method that seeks to sequence a polymer, or indeed any method that measures a property of polymer that is subject to stochastic variations in the order in which the monomers are measured, and in the duration of the event associated with each monomer. The invention also does not require that the polymer remain intact during the measurement process and applies to cases in which the observations are made on multiple individual molecules that are nominally the same.

BRIEF DESCRIPTION OF THE DRAWINGS

FIGS. 6A-6C include illustrative sequencing information generated utilizing the method of the present invention identified as SEQ ID NOS: 1-114.

DETAILED DESCRIPTION OF THE PREFERRED EMBODIMENT

Figure 1:
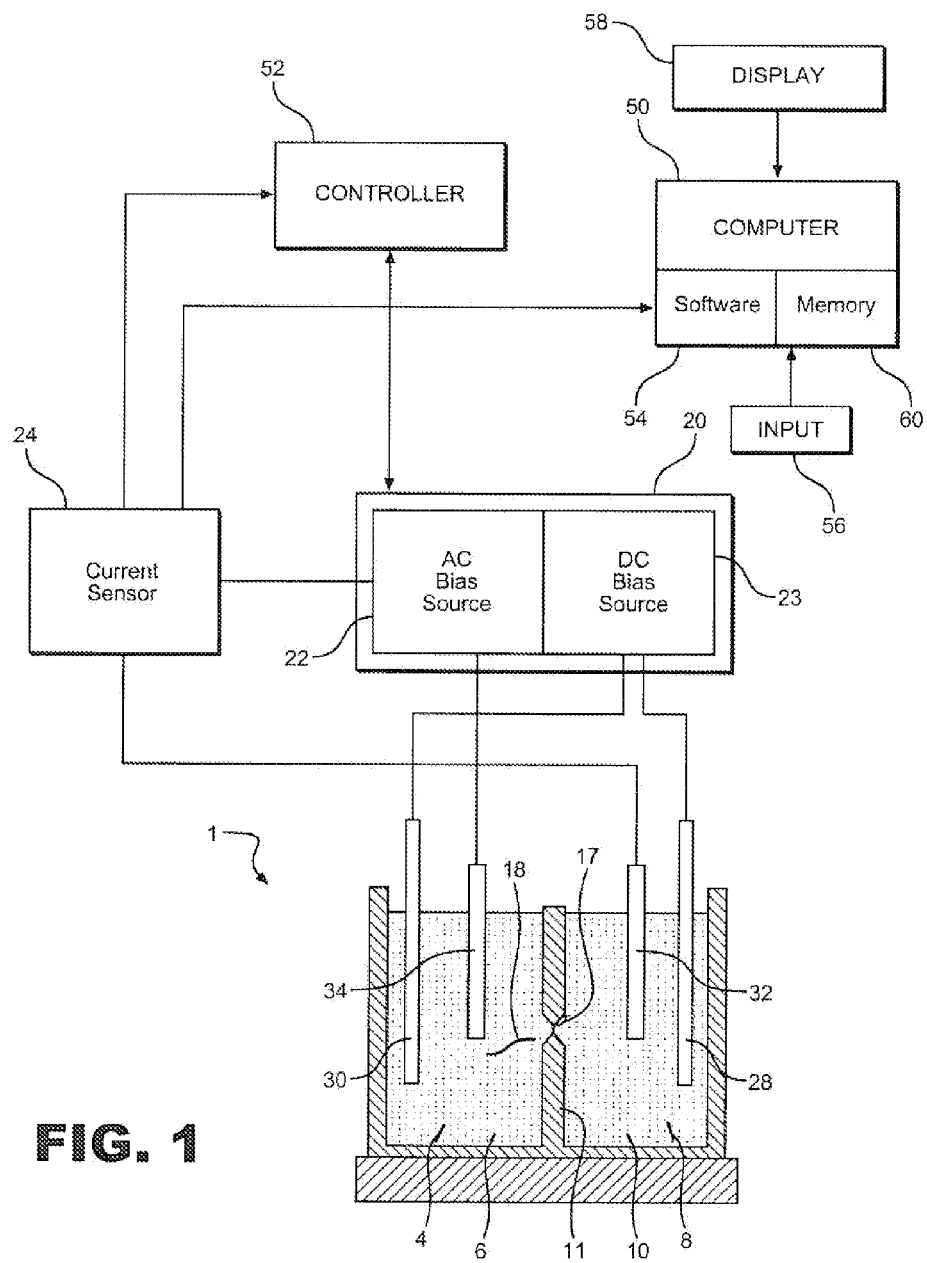
FIG. 1 depicts a polymer sequencing system for use with the method of the present invention.

With initial reference to FIG. 1, a polymer sequencing system or sensing system 1 is utilized in accordance with the present invention. In general, sensing system 1 includes a first fluid chamber or electrolyte bath 4 within which is provided a first solution or electrolyte 6, and a second fluid chamber or sensing volume 8 provided with a second electrolyte 10. Sensing volume 8 is separated from electrolyte bath 4 by a barrier structure 11, which includes a nanopore or nano-scale orifice 17 that provides a fluid path connecting the first and second electrolytes 6 and 10. In one preferred embodiment discussed herein, orifice 17 is in the form of a protein pore embedded in a lipid bilayer across an opening in barrier structure 11 in a manner known in the art.

In general, sensing system 1 controls the translocation of a polymer indicated at 18 through orifice 17 utilizing a translocation means or means for controlling the velocity of a polymer through orifice 17 in the form of a power source 20. In the embodiment shown, translocation power source 20 includes an AC bias source 22 and a DC bias source 23. In addition, a current sensor 24 is provided to measure the AC current through orifice 17 produced by the AC bias source 22. More specifically, current sensor 24 is adapted to differentiate monomers of a polymer on the basis of changes in the electrical current that flows through orifice 17. In a manner known in the art, electrodes 28, 30, 32 and 34 are utilized in conjunction with current sensor 24 and power source 20. A controller 52 may be utilized to control system 1. Current signals detected or measured by current sensor 24 are processed in order to calculate a nominal monomer sequence of polymer 1. For purposes of the present invention, the term "observation" is used to describe measurements of a region of a polymer taken over time utilizing a sensing system, such as sensing system 1. The method of the present invention utilizes two or more repeat observations of the same region of one or more polymers. In general, sensing system 1 is provided for illustrations purposes only, and it should be understood that any equivalent means for detecting individual monomers of a polymer may be utilized in conjunction with the present method.

In accordance with the method of the present invention, sensing system 1 is in communication with means for deducing the sequence of a polymer from the nominal monomer sequences sensed by current sensor 24, such as computer 50. In a preferred embodiment, computer 50 includes software 54 configured to perform the method for deducing the sequence of a polymer of the present invention. Preferably, observations which are determined to have inadequate data quality (e.g., poor measurements) are excluded from the recorded observations processed by the method of the present invention. Computer 50 additionally includes an input device indicated at 56 for entering data, a display 58 for viewing information and a memory 60 for storing information.

The invention applies to polymers in general and to any method that seeks to sequence a polymer by measuring its monomers in a serial manner, but because of its technological significance and large body of existing experimental data, specific examples herein are discussed in terms of sequencing DNA. Further, because of its relative maturity and simplicity among serial-read methods, simulated data for the protein pore current blockade (PPCB) approach of sequencing DNA is utilized in order to illustrate the steps of the invention. However, it should be understood that the method of the present invention is not limited for use with DNA, nor the PPCB measurement method.

Figure 2A:
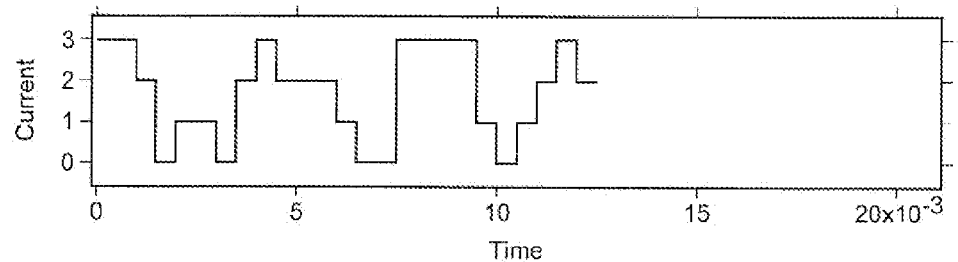
FIG. 2A is a graph depicting a model recording of pore current blockage signals over time for a 25-base ssDNA random sequence.
Figure 2B:
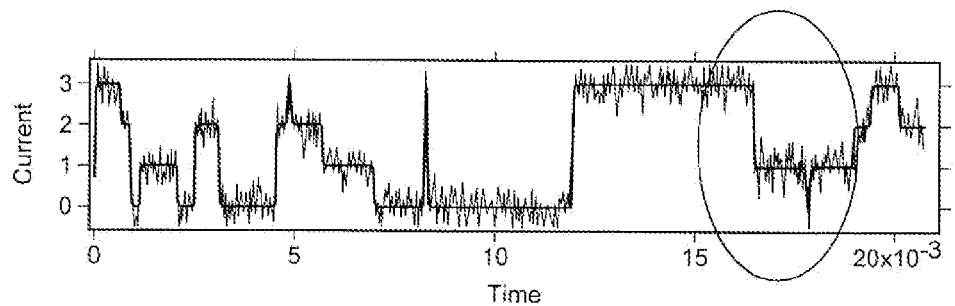
FIG. 2B is a graph depicting a first simulated recording of pore current blockage signals over time for the 25-base ssDNA of FIG. 2A.
Figure 2C:
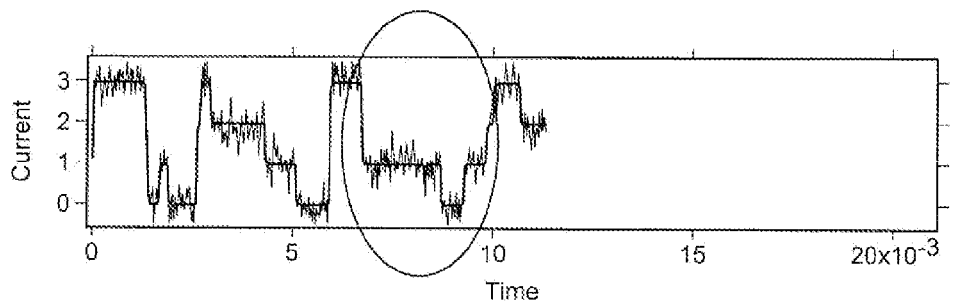
FIG. 2C is a graph depicting a second simulated recording of pore current blockage signals over time for the 25-base ssDNA of FIG. 2A.
Figure 2D:
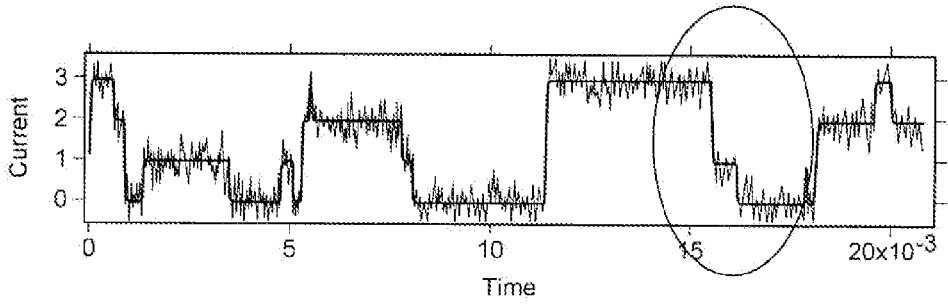
FIG. 2D is a graph depicting a third simulated recording of pore current blockage signals over time for the 25-base ssDNA of FIG. 2A.

In the PPCB approach, a signal indicative of each base is obtained via the reduction in the ionic current passing through pore 17 when a base of polymer or DNA 18 is present in pore 17. FIGS. 2A-2D illustrate the differences that may occur during separate sequencing sessions of the same DNA strand. More specifically, FIG. 2A illustrates a model recording of pore current blockage signals over time, without the effects of noise and diffusion, for a 25-base ssDNA random sequence of CCAGTTGACAAATGGC-CCCTGTACA (SEQ ID NO: 115), wherein for the purposes of illustration, C is assigned a current blocking value of 3, A has a value of 2, G has a value of 0 and T has a value of 1. FIGS. 2B-2D depict three simulated PPCB signal recordings (or observation recordings) as a function of time for the translocating DNA sequence of FIG. 2A, calculated for system parameters of −10° C., 10 kHz bandwidth, 0.33 pArms system noise and a 110 mV DC bias. A fit to each observation recording is shown by the solid line. An example of equivalent regions in FIGS. 2B-2D is given by the ellipses.

It is evident that, while very similar, the mathematically generated records in FIGS. 2B-2D contain differences in duration, despite being for the same input sequence of DNA. These differences arise because of the inherent uncertainties in the stochastic motion of the DNA through the pore. An immediate example is the factor of 2 variations in total translocation time for the three simulated datasets shown in FIGS. 2B-2D. Looking more closely at the graph in FIG. 2C (reading from left to right), we see that the first transition from a 3 pA to 2 pA blockade current is missing as compared to FIGS. 2B and 2D. A second example is the variation in duration of the first 1 pA level in FIGS. 2B-2D. More specifically, in FIG. 2D the duration at this level is approximately 13 times longer than in FIG. 2C, while in FIG. 2B it is approximately equal to the idealized dwell time in FIG. 2A.

Figure 3:
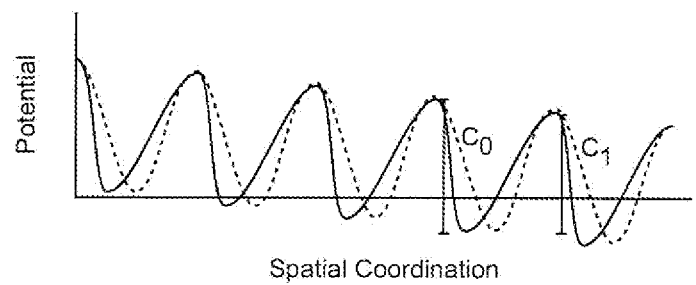
FIG. 3 is a graph of potential vs spatial coordination of a particle being sequenced.

Although individual diffusion events are stochastic, the overall statistical distribution in the case of a diffusion process is well defined. For example, one dimensional diffusion along the axis of a nanopore can be described mathematically as the motion of a rigid particle in a periodic potential. The application of a voltage to pull the DNA through the nanopore corresponds to a tilt in the potential, as shown in FIG. 3. In the limit of large barrier height, the motion can be described as thermally activated hopping from one potential minimum to the next.

The height of the potential barrier (C0, C1) can be determined from the variation of the measured diffusion constant with temperature. For example, for single strand DNA (ssDNA) in the protein pore alpha hemolysin (αHL) the activation energy, E, for a simple series of adenosine (A bases) (at zero potential tilt)=$1.8 \times 10^{-19}$ Joules=108 kJ/mole. At room temperature (20° C.), the value of $1.8 \times 10^{-19}$ Joules is 45 times $k_b T$ (where T is the temperature of the solution in Kelvins and $k_b$ is a constant, known as Boltzmann's constant), which shows that under all likely experimental conditions, ssDNA motion in αHL can be accurately described as thermally activated hopping between minima of the 1-D potential.

A particular impact of being in the thermal activated hopping regime is that the target molecule (e.g., DNA) to be sequenced hops at a time determined by the statistics of thermal activation. Thus, equivalent to the uncertainty in the direction and total number of hops in the position of the target polymer is uncertainty in the time when it moves. This means that whatever time interval is chosen between individual measurements, it is not possible to be certain the molecule has hopped to the next minimum (as desired), hopped to the previous minimum, stayed at the same minimum, or hopped two or more times, skipping one or more bases. To minimize the impact of a hop occurring before a measurement is completed, the measurement time should be minimized. However, it is generally the case that the shorter the measurement time the less accurate the measurement, so there is a practical limit to the data acquisition rate.

Activation over a potential barrier is a paradigm statistical process, the dynamics of which apply to chemical reactions such as enzymes that process DNA. Thus, while new approaches which utilize chemical synthesis or base cutting processes to control the order the bases are measured may seem quite different, in reality, the arrival and dwell time of the bases at the detection zone in these schemes are also subject to random fluctuations in a similar manner as discussed for PPCB-based sequencing. For example, consider the case where the DNA is cut into individual deoxy nucleotide monophosphates (dNMP) at the opening to the pore in a manner that allows the dNMPs to sequentially enter and block the pore. Some dNMPs will escape without blocking the pore and thus be skipped, some dNMP blocking events may happen too close together for both to be resolved (i.e., also skipped), and some may remain bound so long that they are counted as a repeat instance of the same base. In addition, it is not required that the stochastic nature of the disturbance of the base order be specifically thermally activated, and any process that introduces a variation can be addressed by the invention, provided that its statistical distribution can be characterized.

The starting point for the invention is that when the dynamics of the polymer motion are subject to stochastic processes, averaging multiple observations of the same polymer region will lead to meaningless intermediate data values that will only increase the error in identifying the monomers. Accordingly, the present invention utilizes an algorithm to quantize the data into an estimate of the monomer sequence as a first step, and only thereafter incorporates information from additional observations of the same sequence segment.

Figure 4:
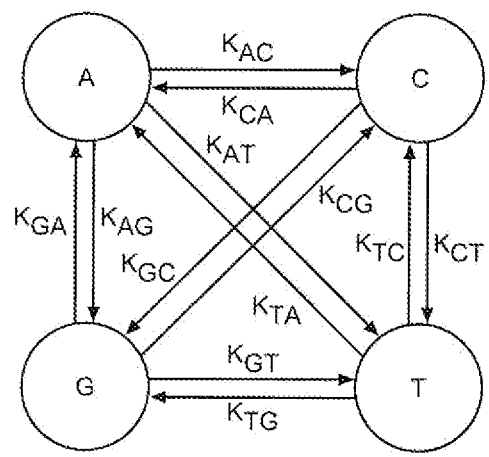
FIG. 4 is a base identification model for use with the present invention.

In the DNA example, if the measurement process has the amplitude of the signal caused by the identity of the single monomer at a sensitive site, one way to quantize the initial data into specific monomers is to apply a simple four state hidden Markov Model (HMM) with one state for each base type (shown in FIG. 4). An HMM is a well known statistical model in which the system being modeled is assumed to be a Markov process with unobserved state. By applying the forward-Viterbi algorithm to each observation, the most likely series of bases can be extracted, along with the time duration the system spends at each base between state changes. The forward algorithm is known to those skilled in the art as an algorithm for computing the probability of a series of observed events. The output of this single base model is thus a sequence in which each base is different.

If the measurement process is such that multiple bases are measured at the same time and contribute to the recorded signal, then this first level model (HMM1) must have more states. For instance, if the sensitive region of the measurement encompasses two base positions, the model must have a state for each possible two base sequence, for a total of sixteen states ($4^n$ states where 4 is the number of base types and n is the estimated number of bases contributing to the measured signal). In this case, the signal produced is likely to have degeneracies (i.e., the base pair AT might produce the same signal as the base pair CG). These degeneracies may be resolved by considering the prior and following signals. For example, if the prior signal indicates the state GA and the following indicates TG, then the state AT is chosen over CG. The output of this two base model will also be a sequence in which each base is different. Conceptually, if the signal is produced by more than two bases, an n base model can be used with a state for each possible n base sequence.

A first estimate of the number of repeat instances of each base can be obtained from the duration the system spends in each state. Alternatively, the number of repeats can be estimated for each monomer at the end of Step 2 (discussed below) from the distribution of observation times for that monomer.

The first step of the algorithm of the present invention is equivalent to algorithms that are commonly utilized for extracting idealized ion channel currents from background noise. However, to improve upon these algorithms we note that, independent of the accuracy in distinguishing bases from one another, there will be errors in the order the bases arrive at the measurement system due to the influence of stochastic processes. Specifically, sensing systems, such as sensing system 1, will occasionally jump to the next base (or further) within the measurement window allocated per base, or step back to a previous base.

To reduce the impact of the above statistical fluctuations, sequencing measurements in accordance with the present invention are performed a total of M times (M≥2) to produce a set of M observations, each observation consisting of a series of measurements. In one embodiment of the invention, the set of M observations can be obtained by measuring different polymers or regions of different polymers containing the same monomer sequence. In other words, multiple observations of the same region of one or more polymers are recorded using sensing system 1. In another embodiment of the invention, the set of M observations can be obtained by measuring the same polymer or region of a polymer multiple times. One method of measuring the same polymer or region of the polymer involves reversing the direction of motion of the polymer through orifice 17 during sequencing. This reversal can be performed repeatedly to record multiple observations of the polymer during both the forward and backward motion of the polymer.

Figure 5:
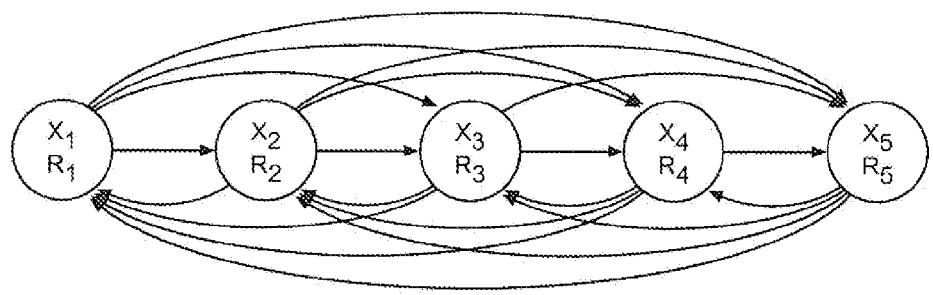
FIG. 5 depicts a Sequence Hidden Markov Model.

For each of the M observations recorded, a first level Hidden Markov Model (HMM1) is utilized to produce a likely sequence of bases or likely monomer sequence. We term each of these M sets of provisional serial base values a trial sequence. If an observation is of poor quality, as judged by the confidence level of the HMM1, or the signal to noise ratio of the measured data, or another metric, the observation can be discarded and additional data collected. We term the chosen set of M trial sequences a complete set of observations. In Step 2 of the method, we then use each of the M trial sequences to construct a Hidden Markov Model representing that sequence. This Sequence Hidden Markov Model (SHMM) is comprised of a base sequence $X_i$, including for each base in the sequence a repeat number as illustrated in FIG. 5. The parameters needed to use the standard HMM algorithms are the transition probabilities $T_{ij}$ defining the probabilities of a transition from state $X_i$ to state $X_j$, the start probabilities $S_i$ defining the probabilities that the first measurement is of state $X_i$, and the observation probabilities $O_{ki}$ defining the probability that we observe the current $I_k$ for duration $D_k$ given that we are in the state $X_i$ with base repeat $R_i$. Also included is a finishing probability that the system exits from the state $X_i$. The SHMM model differs from a strict HMM in that the transition probabilities and the observation probability depend not only on the present state, but also on the direction of the previous hop.

In our example of ssDNA being sequenced by the PPCB method, the probabilities are calculated from the well defined statistical processes of the activated hopping regime and measurements of the diffusion of known polymers. The measurements may indicate that the transition probabilities are dependent on the identity of the monomer being measured, the applied voltage, and on the direction of the motion of the polymer.

For example, the transition probability from state $X_i$ to state $X_j$ consists of two parts. First is the probability of a jump forward or backward, depending only on if i>j or i<j. If |i−j|=1, this is the complete transition probability from state $X_i$ to $X_j$. For |i−j|>1, we must also include the probability that intervening states are skipped over in less than one measurement time. Similarly, the probability of a jump forward or backward depends not only on whether i>j or i<j, but also on the number of base repeats $R_i$ in state $X_i$, and, if $R_i$>1, on whether the last step was forward or backward. For example, for $R_i$=2 we define $P_2$ as the probability of a forward jump given that the system still needs to make two forward jumps to get to the state $X_{i+1}$, and define $P_1$ as the probability of a forward jump given that the system needs to make only one more forward jump to get to the state $X_{i+1}$. From such considerations, we can then derive equations for the probability of a forward jump when the prior jump was forward or backward, respectively, and similar equations for the probability of a backward jump. This can be generalized to higher values of defining $P_k$ as the probability of a forward jump when k forward jumps are needed to reach $X_{i+1}$, leading to a matrix of transition probabilities.

Each of the M SHMMs, each representing one of the M trial sequences, are run through a modified Viterbi algorithm against all of the M observations. This modified Viterbi algorithm is modified from the standard Viterbi algorithm to account for the dependence of the transition and observation probabilities on the direction of the previous step. The output of this modified Viterbi algorithm is the combined probability that the given SHMM produced all of the M observations. By quantifying the probabilities, we can identify the trial sequence, represented by its SHMM, with the highest combined probability as the first iteration $F_1$ in the search for the optimal sequence.

The third step is to systematically alter the $F_1$ sequence to maximize the combined probability of its leading to the M observations. In the simplest embodiment, we postulate that all changes are local, involving only one or two adjacent bases, and at each position we evaluate a small set of likely changes to see if any improves the combined probability. If the combined probability improves, we keep the change and move on. This is done for each position in order, until an entire sweep through the positions results in no further statistically significant improvement. Sequence variations are chosen from a set of statistically most likely changes. The changes used in the first embodiment along with examples of them, are summarized in Table 1 below.

Table 1. Local sequence changes to the $F_1$ used to generate an optimum sequence.

| Change | Description | Permutations | Example |
| --- | --- | --- | --- |
| Base insertion | Insert a nonmatching base before the current base | 2 | AG → ACG or ATG |
| Double insertion | Duplicate current base and following base | 1 | AGCT → AGCGCT |
| Base change | Change the current base to a nonmatching base | 1 or 2 | AGC → ATC AGA → ACA or ATA |
| Base deletion | Delete the current base (Avoiding repeat bases) | 1 or 0 | AGC → AC AGA → AA not allowed |
| Double deletion | Delete the current base and the following base (Avoiding repeat bases) | 1 or 0 | AGCT → AT AGCA → AA not allowed |
| Change base repeat | Change the current base repeat count | Undetermined | A3 → A4 |

As an example, the specific embodiment of the invention described above was run on computer generated data sets of the type shown in FIG. 2. A total of 57 random 25-base sequences were input into the model and 25 possible time records were generated for each of the 57 random input sequence. FIGS. 6A-6C illustrate the 57 trial sequence pairs identified as SEQ ID NOS: 1-114, where the top sequence of each pair shown in FIGS. 6A-6C is the randomly generated "true" sequence, and the lower sequence of each pair shown in FIGS. 6A-6C is the optimum sequence generated by the invention. Characters underlined and in bold indicate the location and nature of an error in the calculated optimum fit.

Although described with reference to a preferred embodiment of the invention, it should be understood that various changes and/or modifications can be made to the invention without departing from the spirit thereof. For example, although an AC current blocking sensor is utilized in the example of a possible means for detecting polymer pore blocking signals, it should be understood that a DC current sensing system or other known monomer detecting system can be utilized with the present invention. In general, the invention is only intended to be limited by the scope of the following claims.

What is claimed is:

1. A method of analyzing a sequential series of measurements of a polymer made during translocation of the polymer through a nanopore, wherein the measurements are dependent on the identity of monomers in the nanopore, the method comprising:
   translocating the polymer through the nanopore;
   making the series of measurements of the polymer while translocating the polymer through the nanopore, wherein the measurements are dependent on the identity of the monomers in the nanopore;
   deriving, from the series of measurements, a first set of serial values; and
   determining differences between the first set of serial values and data generated from the polymer.

2. A method according to claim 1, wherein the first set of serial values is a sequence of monomers.

3. A method according to claim 1, wherein the data generated from the polymer is a plurality of sequential series of measurements of the polymer.

4. A method according to claim 1, wherein determining differences between the first set of serial values and data generated from the polymer includes determining a probability that the first set of serial values could produce the data generated from the polymer.

5. A method according to claim 1, wherein the data generated from the polymer is data stored in a memory in respect of at least one sequence.

6. A method according to claim 5, wherein the data stored in the memory is selected depending upon the polymer to be measured.

7. A method according to claim 5, wherein the data stored in the memory comprises an overall sequence of monomers of a common polymer.

8. A method according to claim 5, wherein said step of determining differences comprises determining differences between the entirety or part of the first set of serial values and the entirety of the data stored in the memory.

9. A method according to claim 5, wherein said step of determining differences comprises determining differences between the entirety or part of the first set of serial values and a part of the data stored in the memory.

10. A method according to claim 5, further comprising determining a sequence of the polymer from which the first set of serial values is derived on the basis of the determined differences.

11. A method according to claim 1, wherein the data generated from the polymer is a second set of serial values.

12. A method according to claim 11, wherein the data generated from the polymer is plural sets of serial values, and the method further comprises identifying sets of serial values that are derived from polymers that are fragments of a common polymer on the basis of differences in overlapping parts of the plural sets of serial values.

13. A method according to claim 12, further comprising constructing an overall set of serial values of the common polymer from the identified sets of serial values of the fragments.

14. A method according to claim 11, wherein the data generated from the polymer is plural sets of serial values, and the method further comprises identifying clusters of sets of serial values and determining that the polymers from which the plural sets of serial values are derived belong to an identified sequence.

15. A method according to claim 10, further comprising counting the numbers of sets of serial values belonging to different sequences.

16. A method according to claim 10, further comprising identifying localized regions where the first set of serial values is dissimilar to the determined sequence of the polymer.

17. A method according to claim 1, wherein the data generated from the polymer comprises data stored in a memory and said step of determining differences comprises determining localized regions where the first set of serial values is dissimilar to the data stored in the memory.

18. A method according to claim 1, wherein
groups of consecutive measurements are dependent on a respective monomer that is different for each group, and
the step of deriving the first set of serial values comprises identifying groups of consecutive measurements, and, in respect of each group, deriving a set of serial values for the group.

19. A method according to claim 18, wherein the values comprise:
an average of the group of measurements;
the period of the group of measurements;
a variance of the group of measurements;
asymmetry information;
confidence information of the measurements;
the distribution of the group of measurements; or
any combination thereof.

20. A method according to claim 1, wherein the polymer is a polynucleotide, and the polymer units are nucleotides.

21. A method according to claim 1, wherein the nanopore is a biological pore.

22. A method according to claim 1, wherein said translocation of the polymer through the nanopore is performed in a ratcheted manner in which successive monomers are registered with the nanopore.

23. A method according to claim 1, wherein the translocation of the polymer is controlled by a molecular ratchet that is a polymer binding protein.

24. A method of estimating the presence, absence or amount of a target polymer, the method comprising
analysing the series of measurements using a method according to claim 1; and
estimating the presence, absence or amount of the target polymer based on the analysis.

25. A method according to claim 24, wherein estimating the presence, absence or amount of the target polymer involves sequencing the target polymer.

26. An analysis device configured to analyze a series of measurements of a polymer made during translocation of the polymer through a nanopore, wherein the measurements are dependent on the identity of monomers in the nanopore, the device comprising:
means for translocating the polymer through the nanopore and making the series of measurements of the polymer while the polymer is being translocated through the nanopore;
means for deriving, from the series of measurements, a set of serial values; and
means for determining differences between the derived set of serial values and data generated from the polymer.

27. A diagnostic device comprising:
an analysis device according to claim 26; and
a measurement system comprising a nanopore through which a polymer is capable of being translocated, the measurement system being arranged to make a series of measurements of the polymer during translocation.

* * * * *

```
                       SEQUENCE LISTING

<160> NUMBER OF SEQ ID NOS: 115

<210> SEQ ID NO 1
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 1
tcggactagc ccttagcaat cgaaa                                             25

<210> SEQ ID NO 2
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 2
tcgactagcc cttagcaatc gaaa                                              24

<210> SEQ ID NO 3
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 3
gtactgggcc cactagctag cacgt                                             25

<210> SEQ ID NO 4
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 4
gtactgggcc cactagctag cacgt                                             25

<210> SEQ ID NO 5
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 5
tcggcttacc attctagaga tgcac                                             25
```

```
<210> SEQ ID NO 6
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 6
tcggacttac cattctagag atgcac                                           26

<210> SEQ ID NO 7
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 7
agtaccttcc ggccctccga ccact                                            25

<210> SEQ ID NO 8
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 8
agtaccttcc ggcccctcga cccact                                           26

<210> SEQ ID NO 9
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 9
attcaatcct caatattgca cctac                                            25

<210> SEQ ID NO 10
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 10
atcaatcctc aaattatgca cctac                                            25

<210> SEQ ID NO 11
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 11
ttcacaacag ctgccatacg ccggg                                            25
```

<210> SEQ ID NO 12
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 12
ttcacaacag ctgccatacg ccggg                                          25

<210> SEQ ID NO 13
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 13
ggggattaac atcctgcact caagc                                          25

<210> SEQ ID NO 14
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 14
gggataacat cctgccactc aagc                                           24

<210> SEQ ID NO 15
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 15
agaattggtt ctcgatagct ctata                                          25

<210> SEQ ID NO 16
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 16
agaatggttt ctcgatagct ctatta                                         26

<210> SEQ ID NO 17
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 17
atagcgatct cgggaagcaa gttgt                                          25

<210> SEQ ID NO 18

```
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 18
atagcgatct cggaagcaag tgtt                                          24

<210> SEQ ID NO 19
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 19
ttccaaggaa ccggtcggta gcaga                                         25

<210> SEQ ID NO 20
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 20
ttccaaggaa ccggtcggta gcaga                                         25

<210> SEQ ID NO 21
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 21
gactcgagct tcggacgtca aacat                                         25

<210> SEQ ID NO 22
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 22
gactcgagct tcgacgtcaa acat                                          24

<210> SEQ ID NO 23
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 23
atgggtatat cctcccgttc tgagt                                         25

<210> SEQ ID NO 24
<211> LENGTH: 25
```

```
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (9)..(10)
<223> OTHER INFORMATION: n is a, c, g, or t

<400> SEQUENCE: 24
atgggtatnn cctcccgttc tgagt                                          25

<210> SEQ ID NO 25
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 25
gcctgggtaa ggaaagcatc tcggc                                          25

<210> SEQ ID NO 26
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 26
gcctgggtaa aggaaagcat ctcgc                                          25

<210> SEQ ID NO 27
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 27
ggaatccaac attctatcgc tggaa                                          25

<210> SEQ ID NO 28
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 28
ggatccaaac attctatcgc tgaa                                           24

<210> SEQ ID NO 29
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 29
ctaaccacag acatctgcgg gaa                                            23
```

```
<210> SEQ ID NO 30
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 30
ctaaaacacc agacatctgc gggaa                                              25

<210> SEQ ID NO 31
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 31
tgttttgtct ggcctagcct acgga                                              25

<210> SEQ ID NO 32
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 32
tgttttgtct ggcctagcct acgga                                              25

<210> SEQ ID NO 33
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 33
cgaaatcata aggaagtcgg accgc                                              25

<210> SEQ ID NO 34
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 34
cgaaatcatt aaggaagtcg ggaccgc                                            27

<210> SEQ ID NO 35
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 35
tcccctactt tagtaaaaca atcac                                              25
```

```
<210> SEQ ID NO 36
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 36
tcccctactt tagtaaaaca tcac                                            24

<210> SEQ ID NO 37
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 37
tttgatacaa taacgcgcta gttcc                                           25

<210> SEQ ID NO 38
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 38
tttgataaca taacgcgcta gttcc                                           25

<210> SEQ ID NO 39
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 39
accatatagt ttattgcaat gtgat                                           25

<210> SEQ ID NO 40
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 40
acattatagt ttatgcaatg ttgaat                                          26

<210> SEQ ID NO 41
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 41
tgcccttcaa tgcactgtgt catgg                                           25

<210> SEQ ID NO 42
```

```
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 42
tgccttcaat gcactgttgt catgg                                            25

<210> SEQ ID NO 43
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 43
ttgccgtccc tataatcatg tgcat                                            25

<210> SEQ ID NO 44
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 44
ttgccgtcct ataatcatgt gcat                                             24

<210> SEQ ID NO 45
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 45
taacctagtg aacgtacttc gagcc                                            25

<210> SEQ ID NO 46
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 46
tactagtgaa cgtacttcga gcc                                              23

<210> SEQ ID NO 47
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 47
gttgacatac aaggttttac tcttg                                            25

<210> SEQ ID NO 48
<211> LENGTH: 24
```

```
<212> TYPE: DNA
<213> ORGANISM: Artificial Sequence
<220> FEATURE:
<223> OTHER INFORMATION: This sequence was randomly generated by a
      computer

<400> SEQUENCE: 48
gtgacataca aggttttact cttg                                          24

<210> SEQ ID NO 49
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 49
ctccgtgcga tattagttgc aaatg                                         25

<210> SEQ ID NO 50
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 50
ctcgtgcgat attagttgca aatg                                          24

<210> SEQ ID NO 51
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 51
gtagccatta gttcgctgac tcccc                                         25

<210> SEQ ID NO 52
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 52
gtagccatta gttcgctgac tcccc                                         25

<210> SEQ ID NO 53
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 53
ggtccgtagt atgtacttca ctgaa                                         25

<210> SEQ ID NO 54
<211> LENGTH: 25
<212> TYPE: DNA
```

<213> ORGANISM: Artificial Sequence
<220> FEATURE:
<223> OTHER INFORMATION: This sequence was randomly generated by a
      computer

<400> SEQUENCE: 54
ggtccgtagt atgtacttca ctgaa                                           25

<210> SEQ ID NO 55
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 55
tacaaatcgg actggagagt gtggg                                           25

<210> SEQ ID NO 56
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 56
tacaaatcgg actgggagag ttgtggg                                         27

<210> SEQ ID NO 57
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 57
agtgcattag atgcgcaccg ccgat                                           25

<210> SEQ ID NO 58
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 58
agtgcattag atgcgcacgc ccgat                                           25

<210> SEQ ID NO 59
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 59
aatcgcgggg taccaaccat ctaag                                           25

<210> SEQ ID NO 60
<211> LENGTH: 24
<212> TYPE: DNA
<213> ORGANISM: Artificial Sequence

```
<220> FEATURE:
<223> OTHER INFORMATION: This sequence was randomly generated by a
      computer

<400> SEQUENCE: 60
aatcgcgggt accaaccatc taag                                            24

<210> SEQ ID NO 61
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 61
agttgcccat ccgcttgggc ttcgc                                           25

<210> SEQ ID NO 62
<211> LENGTH: 22
<212> TYPE: DNA
<213> ORGANISM: Artificial Sequence
<220> FEATURE:
<223> OTHER INFORMATION: This sequence was randomly generated by a
      computer

<400> SEQUENCE: 62
agttgcccat cgcttggctc gc                                              22

<210> SEQ ID NO 63
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 63
cgatatcggc tgaggcctaa cttca                                           25

<210> SEQ ID NO 64
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 64
cgatatcggc tgaggcctaa ctca                                            24

<210> SEQ ID NO 65
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 65
gggatcccta taagcgacga cgccc                                           25

<210> SEQ ID NO 66
<211> LENGTH: 24
<212> TYPE: DNA
<213> ORGANISM: Artificial Sequence
<220> FEATURE:
```

```
<223> OTHER INFORMATION: This sequence was randomly generated by a
      computer
<220> FEATURE:
<221> NAME/KEY: misc_feature
<222> LOCATION: (10)..(12)
<223> OTHER INFORMATION: n is a, c, g, or t

<400> SEQUENCE: 66
gggatcctan nngcgacgac gccc                                            24

<210> SEQ ID NO 67
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 67
agagtggcac taaccaatac gtcga                                           25

<210> SEQ ID NO 68
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (3)..(4)
<223> OTHER INFORMATION: n is a, c, g, or t

<400> SEQUENCE: 68
agnntggcac taaccaatac gtcga                                           25

<210> SEQ ID NO 69
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 69
gtacgggtcg gcccgggcct cccta                                           25

<210> SEQ ID NO 70
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 70
gtacgggtcg gccgggcctc cta                                             23

<210> SEQ ID NO 71
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 71
tagagacggc tagaagtatg gagga                                           25
```

<210> SEQ ID NO 72
<211> LENGTH: 24
<212> TYPE: DNA
<213> ORGANISM: Artificial Sequence
<220> FEATURE:
<223> OTHER INFORMATION: This sequence was randomly generated by a computer
<220> FEATURE:
<221> NAME/KEY: misc_feature
<222> LOCATION: (4)..(5)
<223> OTHER INFORMATION: n is a, c, g, or t

<400> SEQUENCE: 72
tagnnacggc tagaagtatg agga                                           24

<210> SEQ ID NO 73
<211> LENGTH: 25
<212> TYPE: DNA
<213> ORGANISM: Artificial Sequence
<220> FEATURE:
<223> OTHER INFORMATION: This sequence was randomly generated by a computer

<400> SEQUENCE: 73
aacagatagg cttcagaata gtgga                                          25

<210> SEQ ID NO 74
<211> LENGTH: 24
<212> TYPE: DNA
<213> ORGANISM: Artificial Sequence
<220> FEATURE:
<223> OTHER INFORMATION: This sequence was randomly generated by a computer

<400> SEQUENCE: 74
aacagatagg cttcagatag tgga                                           24

<210> SEQ ID NO 75
<211> LENGTH: 25
<212> TYPE: DNA
<213> ORGANISM: Artificial Sequence
<220> FEATURE:
<223> OTHER INFORMATION: This sequence was randomly generated by a computer

<400> SEQUENCE: 75
ctcttaatga cgacctttaa gctgc                                          25

<210> SEQ ID NO 76
<211> LENGTH: 24
<212> TYPE: DNA
<213> ORGANISM: Artificial Sequence
<220> FEATURE:
<223> OTHER INFORMATION: This sequence was randomly generated by a computer
<220> FEATURE:
<221> NAME/KEY: misc_feature
<222> LOCATION: (3)..(5)
<223> OTHER INFORMATION: n is a, c, g, or t

<400> SEQUENCE: 76
ctnnnaatga cgaccttaag ctgc                                           24

<210> SEQ ID NO 77
<211> LENGTH: 25
<212> TYPE: DNA
<213> ORGANISM: Artificial Sequence

```
<220> FEATURE:
<223> OTHER INFORMATION: This sequence was randomly generated by a
      computer

<400> SEQUENCE: 77
ggagccgtac gagagccctt aagcg                                              25

<210> SEQ ID NO 78
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 78
ggagccgtac gagagccctt aagcg                                              25

<210> SEQ ID NO 79
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 79
ccataggcct agatccgtgt tccg                                               24

<210> SEQ ID NO 80
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 80
ccataggcct agatccgttg tccg                                               24

<210> SEQ ID NO 81
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 81
atccgcgaga atccgcagat gttta                                              25

<210> SEQ ID NO 82
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 82
atccgcgaga atccgcagat gttta                                              25

<210> SEQ ID NO 83
<211> LENGTH: 25
<212> TYPE: DNA
<213> ORGANISM: Artificial Sequence
<220> FEATURE:
```

```
<223> OTHER INFORMATION: This sequence was randomly generated by a
      computer

<400> SEQUENCE: 83
atcatatgct gctgcttttc ccgga                                           25

<210> SEQ ID NO 84
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 84
atcatatgct gctgcttttc ccgga                                           25

<210> SEQ ID NO 85
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 85
ccctagtcat cccacttcgt gtaaa                                           25

<210> SEQ ID NO 86
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 86
ccctagtcat cccactttcg ttgtaaa                                         27

<210> SEQ ID NO 87
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 87
gccgagatat tgaatgctaa tactg                                           25

<210> SEQ ID NO 88
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 88
gcgagatatt gaatgctaat actg                                            24

<210> SEQ ID NO 89
<211> LENGTH: 25
<212> TYPE: DNA
<213> ORGANISM: Artificial Sequence
<220> FEATURE:
<223> OTHER INFORMATION: This sequence was randomly generated by a
```

```
         computer

<400> SEQUENCE: 89
gttctcgtga tgggcttgca ctaca                                        25

<210> SEQ ID NO 90
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 90
gtctcgtgat ggcttgcact aca                                          23

<210> SEQ ID NO 91
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 91
gccatgcaac ctgtttcggg ttggc                                        25

<210> SEQ ID NO 92
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 92
gcatgcaacc tgtttcgggt tgc                                          23

<210> SEQ ID NO 93
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 93
actaagcacg gcgcgcgaca agag                                         24

<210> SEQ ID NO 94
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 94
actagcacgg cgctgcgaca agag                                         24

<210> SEQ ID NO 95
<211> LENGTH: 25
<212> TYPE: DNA
<213> ORGANISM: Artificial Sequence
<220> FEATURE:
<223> OTHER INFORMATION: This sequence was randomly generated by a
      computer
```

<400> SEQUENCE: 95
gccaaaccat cacatgccgc cctgg                                          25

<210> SEQ ID NO 96
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 96
gcaaccatca ccatgccgcc tgg                                            23

<210> SEQ ID NO 97
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 97
tccgcagcgc tcagggacga acttg                                          25

<210> SEQ ID NO 98
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 98
tccgcagcgc tcagggacga acttg                                          25

<210> SEQ ID NO 99
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 99
gtacaccatg ctccctgatg cccgt                                          25

<210> SEQ ID NO 100
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 100
gtacaaccat gctccctgat gccgt                                          25

<210> SEQ ID NO 101
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 101
acaaagcgac taaatgcctc cttca        25

<210> SEQ ID NO 102
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 102
acaaagcgac taaatgcctc cttca        25

<210> SEQ ID NO 103
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 103
gagccgcgtg tataaagatt cccag        25

<210> SEQ ID NO 104
<211> LENGTH: 26
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (14)..(17)
<223> OTHER INFORMATION: n is a, c, g, or t

<400> SEQUENCE: 104
gagccgcgtg gtannnngat tcccag        26

<210> SEQ ID NO 105
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 105
caaccgtagt gtaccgaaaa ttcaa        25

<210> SEQ ID NO 106
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 106
caccgtagtg taccgaaaat tcaa        24

<210> SEQ ID NO 107
<211> LENGTH: 25
<212> TYPE: DNA
<213> ORGANISM: Artificial Sequence
<220> FEATURE:

```
<223> OTHER INFORMATION: This sequence was randomly generated by a
      computer

<400> SEQUENCE: 107
gtagtaatat atgtctttcc ggtct                                              25

<210> SEQ ID NO 108
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (11)..(12)
<223> OTHER INFORMATION: n is a, c, g, or t

<400> SEQUENCE: 108
gtagtaatat nngtctttcc ggtct                                              25

<210> SEQ ID NO 109
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 109
cattacttac ggtacggatc actgg                                              25

<210> SEQ ID NO 110
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 110
catacttacg tacggatcac tggg                                               24

<210> SEQ ID NO 111
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 111
tcgtgtgcct tacgtaggga gttgt                                              25

<210> SEQ ID NO 112
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (6)..(7)
<223> OTHER INFORMATION: n is a, c, g, or t

<400> SEQUENCE: 112
tcgtgnncct tacgtaggga gttgt                                              25
```

```
<210> SEQ ID NO 113
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 113
catggagtcg cgttacctag actga                                         25

<210> SEQ ID NO 114
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 114
catgagtcgc gttacctaga ctga                                          24

<210> SEQ ID NO 115
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 115
ccagttgaca aatggcccct gtaca                                         25
```